US012706212B2

(12) United States Patent
Ni et al.

(10) Patent No.: US 12,706,212 B2
(45) **Date of Patent: *Aug. 11, 2026**

(54) MEDICAL EVENT PREDICTION USING A PERSONALIZED DUAL-CHANNEL COMBINER NETWORK

(71) Applicants: NEC Laboratories America, Inc., Princeton, NJ (US); NEC Corporation, Tokyo (JP)

(72) Inventors: Jingchao Ni, Princeton, NJ (US); Wei Cheng, Princeton Junction, NJ (US); Haifeng Chen, West Windsor, NJ (US); Takayoshi Asakura, Tokyo (JP)

(73) Assignee: NEC Corporation (JP)

( * ) Notice: Subject to any disclaimer, the term of this patent is extended or adjusted under 35 U.S.C. 154(b) by 1108 days.

This patent is subject to a terminal disclaimer.

(21) Appl. No.: 17/711,453

(22) Filed: Apr. 1, 2022

(65) Prior Publication Data

US 2022/0319709 A1 Oct. 6, 2022

Related U.S. Application Data

(60) Provisional application No. 63/170,660, filed on Apr. 5, 2021.

(51) Int. Cl.
*G06N 3/08* (2023.01)
*G06N 3/047* (2023.01)
(Continued)

(52) U.S. Cl.
CPC ............. *G16H 50/20* (2018.01); *G06N 3/047* (2023.01); *G06N 3/08* (2013.01); *G16H 10/60* (2018.01); *G16H 20/40* (2018.01); *G16H 50/70* (2018.01)

(58) Field of Classification Search
CPC ........ G16H 50/20; G16H 10/60; G16H 40/67; G16H 50/30; G16H 50/70; G16H 20/40;
(Continued)

(56) References Cited

U.S. PATENT DOCUMENTS

| | | | | |
|---|---|---|---|---|
| 11,990,246 B2 * | 5/2024 | Gupta | .................... | G16H 10/60 |
| 2008/0167567 A1 * | 7/2008 | Bashour | ................. | A61B 5/352 600/521 |

(Continued)

OTHER PUBLICATIONS

Warakagoda et al., Fine-tuning vs full training of deep neural networks for seafloor mine recognition in sonar images, 2017 (Year: 2017).*

(Continued)

*Primary Examiner* — Hien L Duong
(74) *Attorney, Agent, or Firm* — Vincent Duffy

(57) ABSTRACT

Systems and methods for predicting an occurrence of a medical event for a patient using a trained neural network. Historical patient data is preprocessed to generate normalized training samples, and the normalized training samples are sent to a personalized deep convolutional neural network for model pretraining and updating of model parameters. The pretrained model is stored in a remote server for utilization by a local machine for personalization during a preparation time period for a medical treatment. A normalized finetuning set is generated as output, and the model parameters are iteratively finetuned. A personal prediction score for future medical events is generated, and an operation of a medical treatment device is controlled responsive to the prediction score.

20 Claims, 11 Drawing Sheets

(51) Int. Cl.
*G16H 10/60* (2018.01)
*G16H 20/40* (2018.01)
*G16H 50/20* (2018.01)
*G16H 50/70* (2018.01)

(58) Field of Classification Search
CPC ........ G06N 3/047; G06N 3/08; G06N 3/0442; G06N 3/0464; G06N 3/096
See application file for complete search history.

(56) References Cited

U.S. PATENT DOCUMENTS

2013/0185097 A1* 7/2013 Saria ...................... G06Q 10/00 705/3
2015/0045713 A1* 2/2015 Attalah .................. A61B 5/021 706/21
2019/0164285 A1* 5/2019 Nye ....................... G16H 10/60
2020/0160998 A1* 5/2020 Ward .................. G06F 18/2185
2021/0015421 A1* 1/2021 Cicero ................. A61B 5/4509
2021/0042667 A1* 2/2021 Ghosh .................... G16H 50/70
2021/0125091 A1* 4/2021 Fang ...................... G06N 20/10
2021/0225511 A1* 7/2021 Kiraly .................... G06N 20/20
2021/0241871 A1* 8/2021 Burnett .................. G16H 50/70

OTHER PUBLICATIONS

Stack Overflow, "L2 loss vs. mean squared loss", 2019 (Year: 2019).*

De Bois et al., "Adversarial multi-source transfer learning in healthcare: Application to glucose prediction for diabetic people", 2020 (Year: 2020).*

Ivanovic, "Influence of Artificial Intelligence on Personalized Medical Predictions, Interventions and Quality of Life Issues", 2020 (Year: 2020).*

He et al., "An Advanced Two-Step DNN-Based Framework for Arrhythmia Detection", 2020 (Year: 2020).*

Pavlovski et al., "Time-Aware User Embeddings as a Service", 2020 (Year: 2020).*

Zhang et al., Transfer Learning or Self-supervised Learning? A Tale of Two Pretraining Paradigms, 2020 (Year: 2020).*

Shukla, Satya Narayan, et al., "Interpolation-prediction networks for irregularly sampled time series," arXiv preprint arXiv, Sep. 2019, 14 pp. 1909,07782.

Che, Zhengping, et al., "Interpretable deep models for ICU outcome prediction," AMIA annual symposium proceedings, American Medical Informatics Association, Nov. 2016, pp. 371-380, 2016.

Choi, Edward, et al. "Retain: An interpretable predictive model for healthcare using reverse time attention mechanism," Advances in neural information processing systems, Dec. 29, 2016, 9 pages.

Makino, Masaki et al., "Artificial intelligence predicts the progression of diabetic kidney disease using big data machine learning," Scientific reports, Aug. 2019, pp. 1-9, 9.1.

Dovgan, Erik, et al., "Using machine learning models to predict the initiation of renal replacement therapy among chronic kidney disease patients," Plos one, Jun. 2020, pp. 1-18, 15.6.

Inaguma, Dajio, et al. "Prediction model for cardiovascular events or all-cause mortality in incident dialysis patients," PloS one, Aug. 2019, pp. 1-14, 14.8.

* cited by examiner

MEDICAL EVENT PREDICTION USING A PERSONALIZED DUAL-CHANNEL COMBINER NETWORK

RELATED APPLICATION INFORMATION

This application claims priority to provisional application No. 63/170,660, filed Apr. 5, 2021, the contents of which is incorporated herein by reference.

BACKGROUND

Technical Field

The present invention relates generally to predicting an occurrence of a medical event for a patient, and more particularly, to predicting an occurrence of particular medical events for a patient before, during, and after a medical treatment using a trained neural network.

Description of the Related Art

Recently, the tremendous employments of digital systems in hospitals and many medical institutions have brought forth a large volume of healthcare data of patients. The big data are of substantial value, which enables artificial intelligence (AI) to be exploited to support clinical judgement in medicine. As one of the critical themes in modern medicine, the number of patients with kidney diseases has raised social, medical and socioeconomic issues worldwide. Hemodialysis, or simply dialysis, is a process of purifying the blood of a patient whose kidneys are not working normally, and is one of the important renal replacement therapies (RRT). However, dialysis patients are at high risk of cardiovascular and other diseases, and thus require intensive management on blood pressure, anemia, mineral metabolism, etc. Otherwise, patients may encounter critical events, such as low blood pressure, leg cramp, and even mortality, during dialysis and/or other medical treatments.

SUMMARY

A computer implemented method for predicting an occurrence of a medical event for a patient using a trained neural network by preprocessing received historical patient data for a plurality of patients to generate a plurality of normalized training samples. Normalized training samples are sent to a personalized deep convolutional neural network (P-DCCN) for model pretraining and updating of model parameters using the P-DCCN, the pretrained model is stored in a remote server for utilization for personalization by a local machine during a preparation time period for a medical treatment, and a normalized finetuning set is generated as output from the P-DCCN by processing input personal data for the patient from the local machine. Model parameters of the P-DCCN are iteratively finetuned by performing a plurality of training iterations using the generated normalized finetuning set. A personalized prediction score for future medical events for the patient is generated using the P-DCCN, and an operation of a medical treatment device is controlled responsive to the personalized prediction score for future medical events.

A system for predicting an occurrence of a medical event for a patient using a trained neural network by preprocessing, using a processor operatively coupled to a computer-readable storage medium, received historical patient data for a plurality of patients to generate a plurality of normalized training samples. Normalized training samples are sent to a personalized deep convolutional neural network (P-DCCN) for model pretraining and updating of model parameters using the P-DCCN, the pretrained model is stored in a remote server for utilization for personalization by a local machine during a preparation time period for a medical treatment, and a normalized finetuning set is generated as output from the P-DCCN by processing input personal data for the patient from the local machine. Model parameters of the P-DCCN are iteratively finetuned by performing a plurality of training iterations using the generated normalized finetuning set. A personalized prediction score for future medical events for the patient is generated using the P-DCCN, and an operation of a medical treatment device is controlled responsive to the personalized prediction score for future medical events.

A non-transitory computer-readable storage medium including a computer-readable program for predicting an occurrence of a medical event for a patient using a trained neural network by preprocessing received historical patient data for a plurality of patients to generate a plurality of normalized training samples. Normalized training samples are sent to a personalized deep convolutional neural network (P-DCCN) for model pretraining and updating of model parameters using the P-DCCN, the pretrained model is stored in a remote server for utilization for personalization by a local machine during a preparation time period for a medical treatment, and a normalized finetuning set is generated as output from the P-DCCN by processing input personal data for the patient from the local machine. Model parameters of the P-DCCN are iteratively finetuned by performing a plurality of training iterations using the generated normalized finetuning set. A personalized prediction score for future medical events for the patient is generated using the P-DCCN, and an operation of a medical treatment device is controlled responsive to the personalized prediction score for future medical events.

These and other advantages of the invention will be apparent to those of ordinary skill in the art by reference to the following detailed description and the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
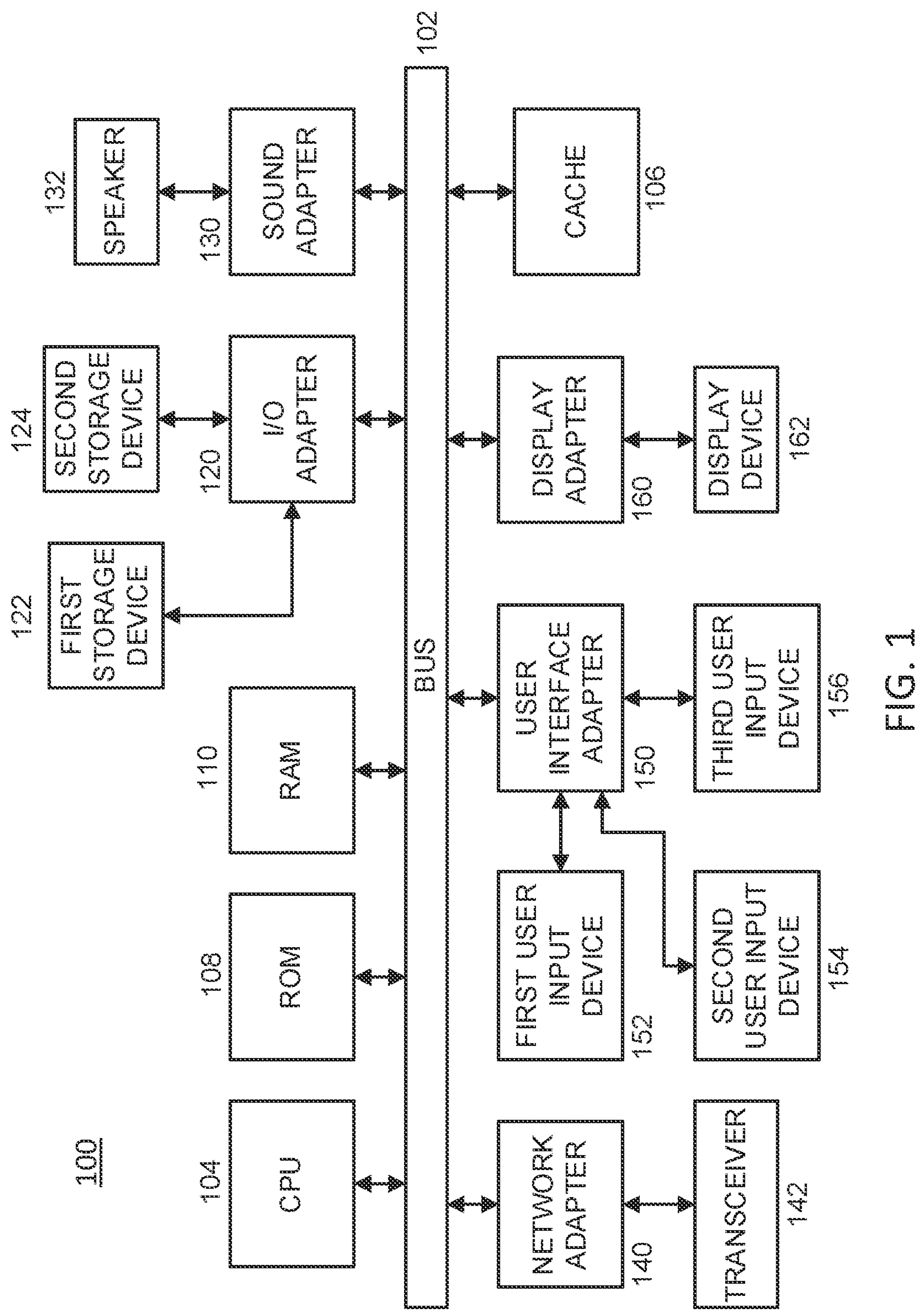
FIG. 1 is a block/flow diagram illustrating an exemplary processing system to which the present principles may be applied, in accordance with the present principles.

In accordance with various embodiments of the present principles, systems and methods are provided for predicting disease treatment events using a personalized dual-channel combiner network (P-DCCN).

In a particularly useful embodiment, a system and method for predicting an occurrence of particular medical events for a patient before, during, and after a medical treatment (e.g., dialysis treatment) using a trained neural network is provided in accordance with embodiments of the present invention.

As noted above. Hemodialysis, or simply dialysis, is a process of purifying the blood of a patient whose kidneys are not working normally, and is one of the important renal replacement therapies (RRT). However, dialysis patients are at high risk of cardiovascular and other diseases, and thus require intensive management on blood pressure, anemia, mineral metabolism, etc. Otherwise, patients may encounter critical events, such as low blood pressure, leg cramp, and even mortality, during dialysis and/or other medical treatments. Therefore, medical staff decides how to proceed with dialysis from various viewpoints based on patient risks, potential treatment events, and variable clinical factors related to dialysis events. Given the availability of big medical data, the present invention leverages AI systems using a dual-channel combiner network (DCCN) for making prognostic prediction scores during the pre-dialysis period on the incidence of events in future dialysis, which can largely facilitate the decision-making processes of medical staffs, and hence reduce the risk of harmful and/or undesired medical events.

However, two key challenges prevent conventional AI systems to be successfully applied for precise analysis of medical data of patients: (1) due to the privacy of data, usually it is difficult to obtain a large amount of patients' data from hospitals that are sufficient for training an accurate model; and (2) due to the high variety of the population among patients, it is difficult for a single pre-trained model to be accurate for every new patient, who are generally different in their age, gender, genetics, health conditions, etc., from the patients data in the training set. As such, a conventional single pre-trained model that is trained a limited training dataset is not generalizable for predictive analysis on data of new patients.

In accordance with various embodiments, the present invention harnesses the potential of the management data of dialysis patients by training and utilizing a neural network (e.g., Deep Neural Network (DNN). DCCN, etc.), and thus providing automatic, high-quality, and particularly, personalized prognostic prediction scores on the incidence of events during dialysis, through a new pretraining and finetuning strategy. By personalizing a pre-trained model for every patient using a small amount of finetuning data, the model are able to alleviate the aforementioned two challenges and be generalized well to testing dataset and be utilized on patients undergoing medical procedures (e.g., dialysis) to minimize risks and maximize benefits of the procedures for particular patients.

The present invention is a P-DCCN system/method which provides a systematic and data driven solution to medical event (e.g., dialysis event) prediction not known in the art. The present invention is a neural network based intelligent computing system that does not require human efforts or feature engineering. The present P-DCCN system/method can include a dual-channel component for integrating static features, low frequent temporal features, and comparatively high frequent temporal features for joint representation learning and the prediction of dialysis events during treatment. In various embodiments, the present invention utilizes a pre-training and finetuning strategy that addresses and alleviates the challenges of insufficient training data, and the distribution discrepancy of patients data, and thus delivers much higher efficiency of processing and accuracy over conventional models without personalization. This property makes P-DCCN remarkably different from other models with conventional neural network training strategies.

In some embodiments, a pretraining component of the P-DCCN system can be utilized on historical records of a comparatively small amount of a patient's overall medical record data, and can generate a pretrained model that can be stored on server or cloud platform for use for future new patients predictive analysis. The finetuning component of the P-DCCN system can send the pre-trained model to local devices where new patients' records are stored for finetuning. This component only uses a comparatively small amount of new records, similarly to the pretraining component described above. With such a small amount of data for personalization, the model can achieve significant improvement of accuracy and decreased processor requirements as compared to conventional, non-personalized systems and methods.

In some embodiments, a dialysis recording data processing component of a DCCN system transforms the historical records of each patient into static profile features and time series features of different frequencies, which can be input to DCCN computing component for further training and/or processing. The deep neural network design of the P-DCCN computing component improves prediction accuracy and greatly reduces required human efforts on feature engineering, in accordance with aspects of the present invention. In some embodiments, the dual-channel design of the P-DCCN computing component can include a multilayer perceptron (MLP) and a long short-term memory (LSTM) recurrent neural network, which can integrate both static features and temporal features of different frequencies for joint event prediction, in accordance with aspects of the present invention.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Referring now to the drawings in which like numerals represent the same or similar elements and initially to FIG. 1, an exemplary processing system 100, to which the present principles may be applied, is illustratively depicted in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Moreover, it is to be appreciated that systems 100, 200, 400, 500, 501, 700, 800, and 1000, described with respect to FIGS. 1, 2, 4, 5A, 5B, 7, 8, and 10, respectively, are systems for implementing respective embodiments of the present principles. Part or all of processing system 100 may be implemented in one or more of the elements of systems 200, 400, 500, 501, 700, 800, and 1000, according to various embodiments of the present principles.

Further, it is to be appreciated that processing system 100 may perform at least part of the method described herein including, for example, at least part of methods 300, 400, 500, 501, 600, 700, and 900 of FIGS. 3, 4, 5A, 5B, 6, 7, and 9, respectively. Similarly, part or all of systems 200, 400, 500, 501, 700, 800, and 1000 may be used to perform at least part of methods 300, 400, 500, 501, 600, 700, and 900 of FIGS. 3, 4, 5A, 5B, 6, 7, and 9, respectively, according to various embodiments of the present principles.

Figure 2:
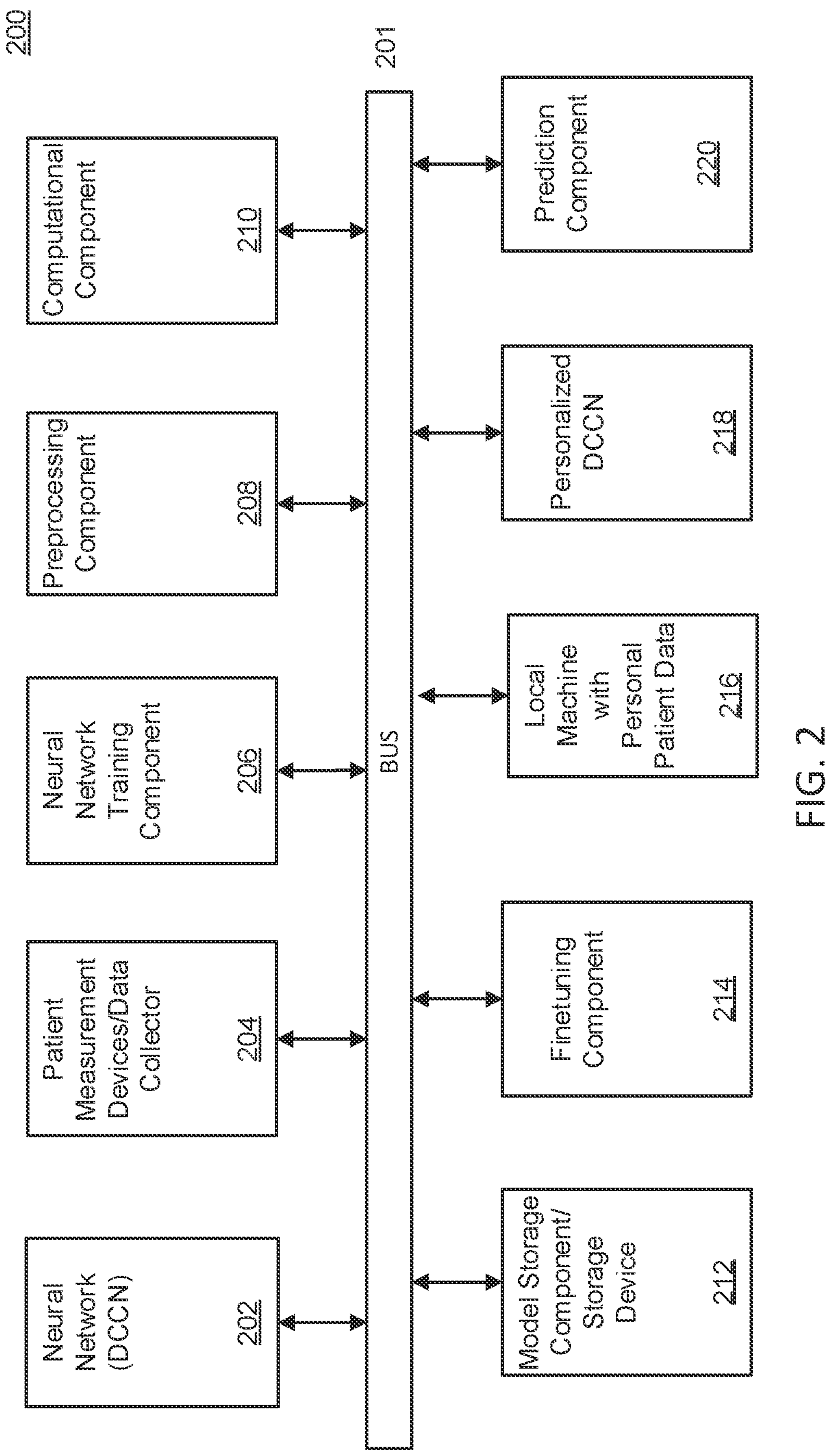
FIG. 2 shows a diagram of a system/method for predicting disease treatment events using a personalized dual-channel combiner network (P-DCCN), in accordance with an embodiment of the present principles.

Referring now to FIG. 2, a block diagram showing a system/method 200 for predicting disease treatment events using a personalized dual-channel combiner network (P-DCCN) 218 is illustratively depicted in accordance with an embodiment of the present principles. In one embodiment, a dual-channel combiner network (DCCN) 202 may be utilized to generate a personalized DCCN (P-DCCN) 218 by training a DCCN 202 using a neural network training component 206. The training component 206 may include a preprocessing component 208 (e.g., for pretraining), a computational component 210 (e.g., for processing static and temporal features), a model storage component 212 (e.g., storage device), a finetuning component 214, which can adapt a globally pretrained model to a particular patient, based on, for example, historical and/or real-time patient measurement devices taken using a patient measurement device 204 and other personal patient data gathered and stored on a local machine 216, in accordance with aspects of the present invention.

In various embodiments, after the finetuning is completed using the finetuning component 214, a prediction component 220 can predict future events (e.g., medical treatment events, adverse patient health events, etc.) for a particular patient using the trained P-DCCN, in accordance with aspects of the present invention. It is to be appreciated that the components of the system 200 may be connected by a bus 201 or may be connected via any suitable communication means (e.g., wireless connection, remote connection across the Internet, wired Ethernet connection, other wired connection, etc.), in accordance with aspects of the present invention.

Figure 3:
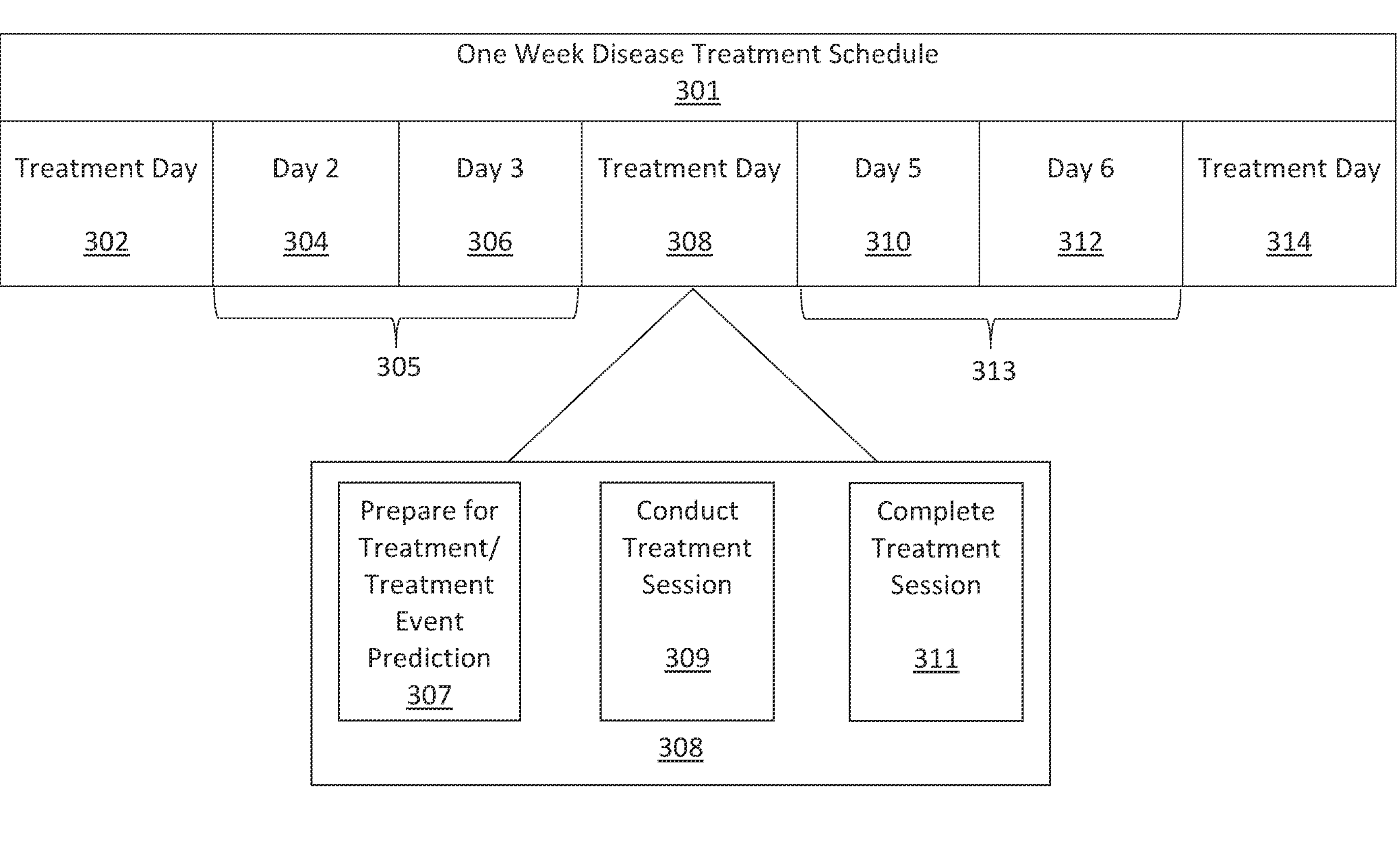
FIG. 3 shows a block/flow diagram showing exemplary time periods for prediction of disease treatment events, disease treatment preparation and disease treatment events, in accordance with an embodiment of the present principles.

Referring now to FIG. 3, a block/flow diagram showing exemplary time periods for prediction of disease treatment events, disease treatment preparation and disease treatment events 300 is illustratively depicted in accordance with an embodiment of the present principles.

Medical patients often have a regular routine of receiving treatment for an ailment (e.g., dialysis), generally with treatment at least once per week, depending on the type and/or severity of the ailment. For ease of illustration, the present invention will be described with reference to dialysis treatment for a patient, although it is to be appreciated that the present principles can be applied to predict medical events for any sort of ailment/disease before, during, and after treatment, in accordance with various embodiments of the present invention.

Dialysis patients generally have regular routine of dialysis sessions with a frequency of 3 times per week, with each session taking 4 to 5 hours. An exemplary one-week schedule 301 for a dialysis patient can include a treatment day 302, day 2 304 and day 3 306 as non-treatment days, a second treatment day 308, day 5 310 and day 6 312 as non-treatment days, and a third treatment day 314. As discussed above, various detrimental medical events could occur before, during, and/or after a dialysis treatment, and thus, the present invention minimizes a risk of detrimental health effects before, during, and/or after a dialysis treatment by predicting the possibility of the incidence of events in a near future dialysis session (e.g., predict events prior to dialysis treatment session) for each patient based on the past recording data utilizing a P-DCCN, in accordance with embodiments of the present invention.

Historical recording data of dialysis patients mainly constitutes four parts: static profiles of the patients (e.g., age, gender, starting time of dialysis, etc.), dialysis measurement records (with a frequency of 3 times per week (e.g., blood pressure, weight, venous pressure, etc.), blood test measurements (with a frequency of 2 times per month (e.g., albumin, glucose, platelet count, etc.), and cardiothoracic ratio (CTR) (with a frequency of 1 time per month). The last three parts are dynamic and change over time, so they can be modeled by time series, but with different frequencies, in accordance with aspects of the present invention.

The present invention is an artificial intelligent system, built upon a building block architecture of dual-channel neural networks called dual-channel combiner network (DCCN), which integrates the aforementioned different parts of the data for model training and prognostic score predictions, and will be described in further detail herein below.

In accordance with embodiments of the present invention, during a treatment day 302, 308, 314, dialysis events (e.g., medical events which can occur during dialysis treatment session 309) can be predicted during the time period for preparation for treatment 307 prior to conducting the treatment session 309. The treatment session can be completed in block 311, and measurements and other patient data can be utilized for further training of the P-DCNN for use at future dialysis treatment sessions (e.g., treatment day 314) in accordance with embodiments of the present invention.

Figure 4:
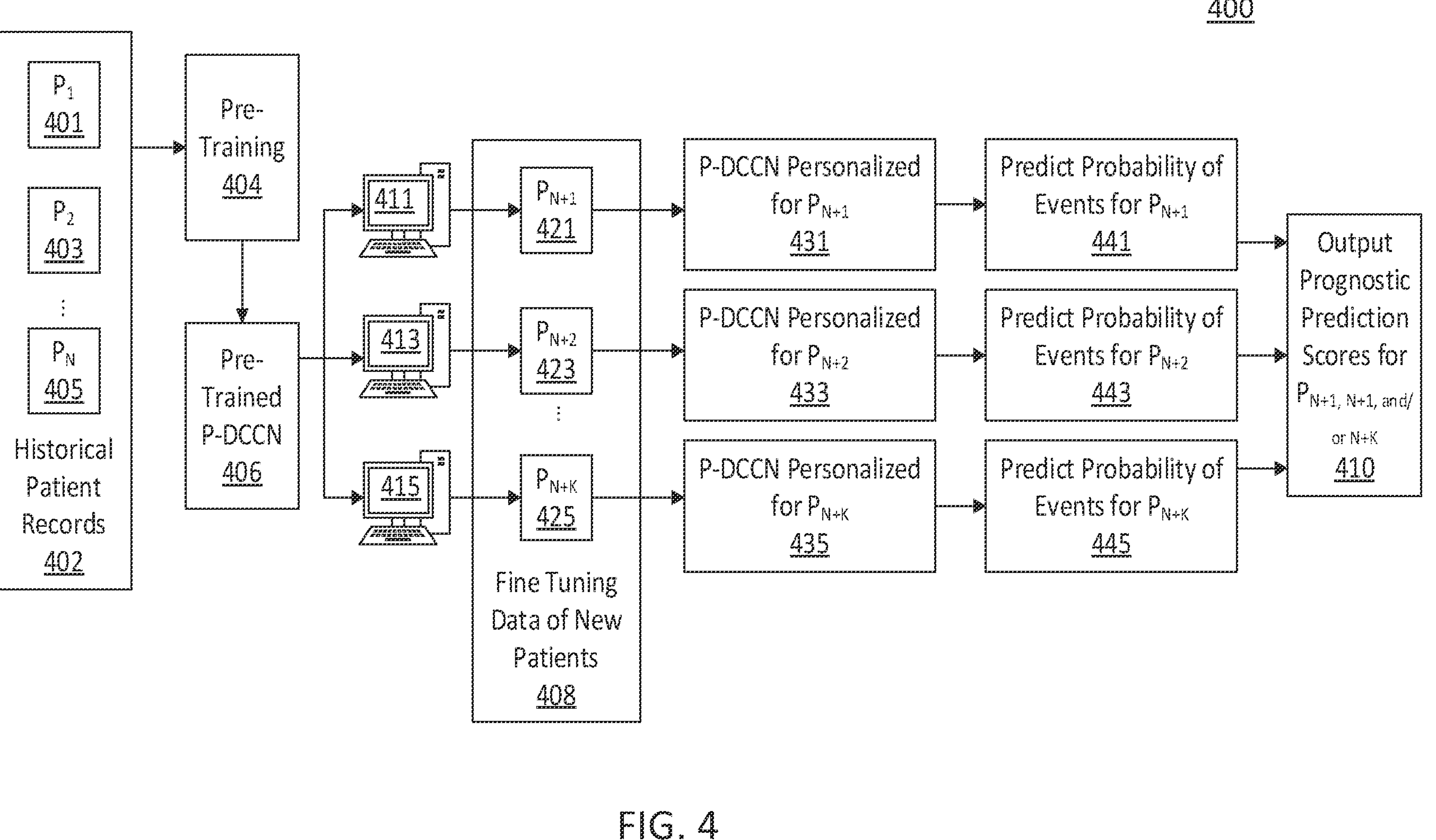
FIG. 4 shows a diagram of a system/method for predicting disease treatment events using a personalized dual-channel combiner network (P-DCCN), in accordance with an embodiment of the present principles.

Referring now to FIG. 4, a block diagram of a system/method 400 for predicting disease treatment events using a personalized dual-channel combiner network (P-DCCN) is illustratively depicted in accordance with an embodiment of the present principles.

In some embodiments, the present invention is an artificial intelligence system, built upon a building block architecture of a dual-channel neural network called a dual-channel combiner network (DCCN), which integrates the aforementioned different parts of the data for model training and prognostic score predictions. In various embodiments, the present invention can generate a personalized DCCN (P-DCCN) for data for all individual patients by utilizing a pretraining and finetuning framework, which is described in further detail herein below, in accordance with aspects of the present invention.

In some embodiments, historical patient records 402 for N patients (e.g., $P_1$ 401. $P_2$ 403, . . . , $P_N$ 405) can be received as input for pretraining 404 to generate a pretrained P-DCCN 406 in accordance with aspects of the present invention. In the pretraining stage 404, the P-DCCN 406 can be trained using historical record data of a plurality of different patients 402, which can be acquired from a database (e.g., Electronic Health Record (EHR) database), from hospital records for individual patients, etc. The historical patient records 402 can include, for example, a patient profile, dialysis measurements, blood test measurements, CTR measurements, etc., which can be utilized as input for training the pretrained P-DCNN 406 in accordance with aspects of the present invention.

In some embodiments, the pretrained P-DCCN 406 can be stored on a server or cloud platform (not shown) for use in further processing. The pretrained P-DCCN 406 can be sent to one or more of a plurality of local machines 411, 413, 415 by any suitable data transport means (e.g., wireless, wired, remote connection, etc.) for fine tuning data of one or more of a plurality of K new patients (e.g., $P_{N+1}$ 421, $P_{N+2}$ 423, . . . , $P_{N+K}$ 425) in block 408. At the finetuning stage 408, once a new patient has accumulated certain amount of medical record data (e.g., a comparatively small amount from a patient's overall medical record), such as several weeks of records, these records can be used to finetune the pre-trained P-DCCN 406 for personalization for particular patients.

In some embodiments, the generated, trained personalized P-DCNNs (e.g., $P_{N+1}$ 431, $P_{N+2}$ 433, . . . , $P_{N+K}$ 435) can be used for future predictive analysis for the respective particular patients to predict a probability of medical events occurring before, during, and/or after a medical treatment in blocks 441, 443, and 445, respectively. Such personalization of the P-DCNN improves accuracy over conventional models, which do not contemplate such personalization. In block 410, the prediction scores determined in blocks 441, 443, and 445 can be output prior to treatment, during treatment, and/or after treatment of a patient, in accordance with aspects of the present invention. As many medical treatments (e.g., dialysis treatment) can be required over a long period of time (e.g., months, years, life-long, etc.), the P-DCCN 406 can be continuously finetuned in block 408 and personalized for improved accuracy iteratively throughout the treatment of the patient. It is noted that although the present invention was described above with regard to dialysis treatment, it is to be appreciated that the P-DCCN system and method of the present invention can be applied to other medical record data, diseases, and/or medical treatment procedures, in accordance with various embodiments of the present invention.

Figure 5A:
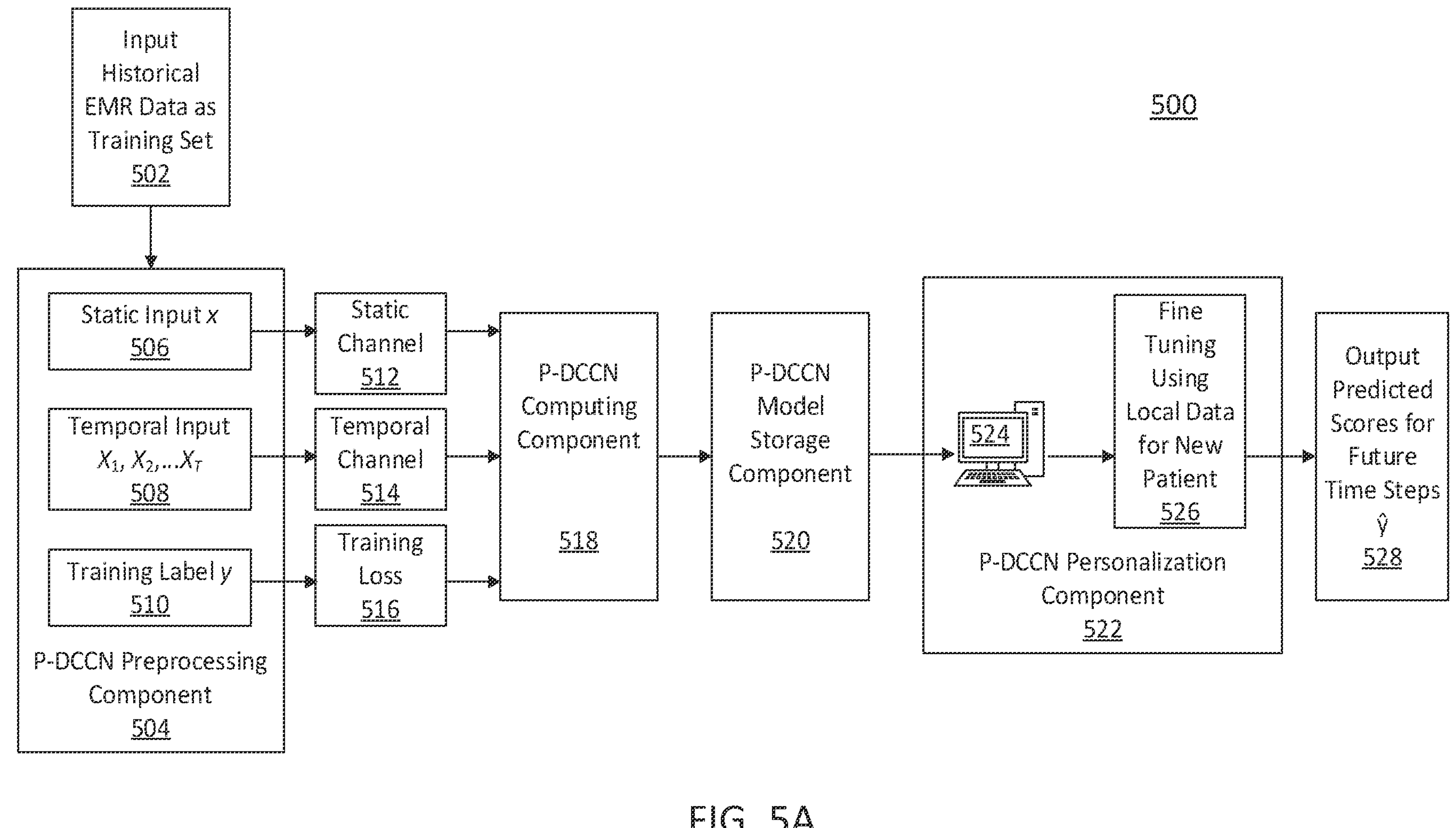
FIG. 5A shows a diagram of a system/method for predicting disease treatment events using a personalized dual-channel combiner network (P-DCCN), in accordance with an embodiment of the present principles.

Referring now to FIG. 5A, a high-level diagram of a system/method 500 for predicting disease treatment events using a personalized dual-channel combiner network (P-DCCN) is illustratively depicted in accordance with an embodiment of the present principles.

In accordance with embodiments of the present invention, historical medical records (e.g., historic electronic medical records (EMR)) can be input as a neural network training set in block 502 for use by the P-DCNN data preprocessing component 504. The historical records of dialysis patients can be stored in any suitable form (e.g., cvs, excel, etc.). Each patient can have a file that includes medical information on a static profile (e.g., age, gender, starting time of dialysis, etc.), which can be input as static input X in block 506. The file may also include medical information on a temporal profile (e.g., (e.g., dialysis measurements, blood test measurements, event incidences, albumin, glucose, platelet count, etc.), which can be input as temporal input $X_1, X_2, \ldots, X_T$ in block 508, in accordance with aspects of the present invention. Each row can indicate a particular date of a hospital visit by the patient. In some embodiments, the static input 506 and the temporal input 508 can be sent to a P-DCCN computing component 518 using a static channel 512 and a temporal channel 514, respectively, for further training and/or processing, in accordance with aspects of the present invention.

In some embodiments, each column can indicate a particular feature, such as some indicator metrics in the dialysis measurements (e.g., blood pressure, weight, venous pressure, etc.). Since different parts have different frequencies, some entries in the form can be blank indicating that feature is not measured at a particular date, in accordance with aspects of the present invention. In block 510, a training label y can be generated, and sent as input including training loss in block 516 to a P-DCCN computing component 518, which will be described in further detail herein below with reference to FIG. 5B.

In various embodiments, the P-DCCN preprocessing component 504 can extract different parts of the data from the files, removes noisy information, and fills in missing values by using mean values of the corresponding features in the historical data and/or by using values from adjacent earlier time steps, in accordance with aspects of the present invention.

In some embodiments, the preprocessing component 504 can set up a time window of width w to segment the time series data, which is described in further detail herein below with reference to FIG. 6. In an embodiment, each time window can generate a sample X from time step T−w to time step T. and can associate it with an event label Y at time step T+1. This generates a sample's focus on the features at the comparatively closest dates to a future event. Because different parts have different frequencies, all dialysis measurements in the time window can be included, while the blood test measurements on the closest date to the time window can also be included. Then the time window can slide from the beginning of the date to the end of the date in the records to generate multiple samples.

In an embodiment, after samples are generated, the preprocessing component 504 can normalize all samples using Gaussian normalization method such that the features of the training samples have mean of 0 and variance of 1, which facilitates the stability of the computing component algorithm in block 518. For testing samples, they can be normalized by using the mean and variance obtained from the training data in block 518, and the normalized samples can be sent to the model storage component 520 for further model training, testing, and/or storage, in accordance with aspects of the present invention. In various embodiment, the P-DCCN computing component 518 can include two channels, namely a static channel for processing static and comparatively low frequency temporal features, and a temporal channel for processing comparatively high frequency temporal features, which is described in further detail herein below with reference to FIG. 5B, in accordance with aspects of the present invention.

In some embodiments, a P-DCCN model storage component 520 can receive a pretrained P-DCCN model as input from the P-DCCN computing component 518, and the pretrained model can be trained using input historical records 502 of a particular (e.g., threshold) amount of a patient's data provided as the training set. This process can update the parameters of P-DCCN to fit the data in the training set, so that it can extract sufficient knowledge that can be further finetuned and personalized in block 526 using data from a local machine 524 and a P-DCCN personalization component 522, in accordance with aspects of the present invention.

In various embodiments, the P-DCCN model can be pre-trained using an optimizer with a regression loss function in block 518 as follows:

$$l = \frac{1}{N}\sum_{i=1}^{N}\|\hat{y}_i - y_i\|_2^2 + \lambda\|\theta\|_2^2$$

where $y_i$ is a true indicator of the incidence of an event for the i-th sample in the training data. It is 1 if there is an event, and 0 otherwise. $\hat{y}_1$ is the predicted score for the i-th sample. N is the total number of the training samples. θ represents the model parameters. λ is a hyperparameter to control the regularization on model parameters for avoid overfitting during the training process.

After pre-training is done in block 518, the pre-trained P-DCCN (with all parameters updated and fixed) can be sent to a server or a cloud platform for storage in block 520, so that it can be easily distributed to one or more local machines 524 for further finetuning and personalization in block 526 using a comparatively small amount of records from new patients that are collected by the local machines, in accordance with aspects of the present invention.

In practice, when a new patient has been attending dialysis treatments for several weeks, the local machine 524 collects a plurality of different types of records (e.g., static and temporal measurements) for that patient during the time. Although the amount of records collected by the local machine 524 is much smaller than the data size in the pre-training dataset, these records are specific to the particular patient and thus are valuable to adapt the globally pre-trained model to the contexts of the particular patient. This personalization process using the P-DCCN personalization component in block 522 via a comparatively small amount of finetuning data leverages the advantages of the few-shot learning, in accordance with aspects of the present invention.

In some embodiments the pre-trained P-DCCN stored in the model storage component 520 can be sent to a local machine 524 where the finetune dataset can be collected and stored locally. The finetune dataset is again preprocessed during the fine tuning in block 526, similarly to the preprocessing described above with reference to the preprocessing component 504 for generating training samples.

In some embodiments, the pre-trained P-DCCN can be finetuned in block 526 using an optimizer with a regression loss function described above in Section 3:

$$l = \frac{1}{N'}\sum_{i=1}^{N'}\|\hat{y}_i - y_i\|_2^2 + \lambda\|\theta\|_2^2$$

where N' here represents the total number of samples in the finetuning set, which is smaller than N, the number of samples in the pre-training set, where $y_i$ is a true indicator of the incidence of an event for the i-th sample in the training data. It is 1 if there is an event, and 0 otherwise. $\hat{y}_i$ is the predicted score for the i-th sample. N is the total number of the training samples. θ represents the model parameters. λ is a hyperparameter to control the regularization on model parameters for avoid overfitting during the training process.

In some embodiments, once the finetuning in block 526 is done, the personalized model P-DCCN can be used to predict future events for the particular patient by outputting prediction scores for particular events for future time steps Y based on analysis of the patient's historical records data received as input from the local machine 524 and the input historical EMR data in block 502. Predictions obtained in this manner in block 528 are significantly more accurate than using the pre-trained model directly at least in part because the model is adapted to the particular patient's data so that the distribution discrepancy between the particular patient's data and the data of the pre-training set is alleviated, in accordance with aspects of the present invention.

Figure 5B:
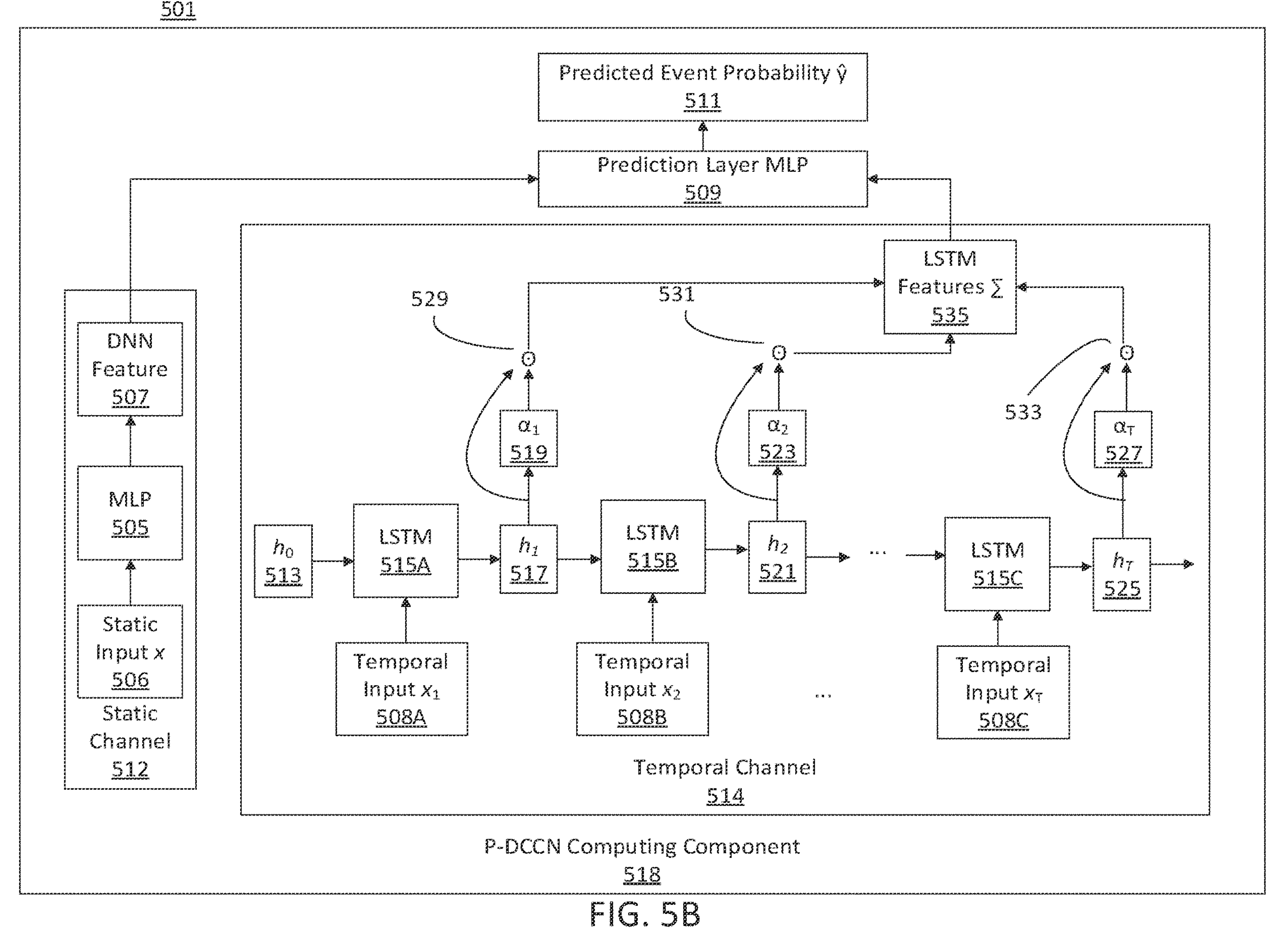
FIG. 5B shows a diagram of a system/method for predicting disease treatment events using a personalized dual-channel combiner network (P-DCCN) computing component, in accordance with an embodiment of the present principles.

Referring now to FIG. 5B, a diagram 501 of a personalized dual-channel combiner network (P-DCCN) computing component 518 for predicting disease treatment events is illustratively depicted in accordance with an embodiment of the present principles.

In various embodiments, the P-DCCN computing component 518 can include two channels, namely a static channel 512 for processing static and comparatively low frequency temporal features, and a temporal channel 514 for processing comparatively high frequency temporal features, in accordance with aspects of the present invention.

In some embodiments the static channel 512 can receive static features (e.g., liquid temperature, hourly water removal rate, target amount of water removal, dry weight, weight after last dialysis treatment, time before dialysis weight measurement, gain of this time period, etc.) as static input x 506. The static features, and comparatively low frequency temporal features, can be represented by a vector $x_s$, and the static channel 512 can include a multilayer perceptron 505 (MLP) to encode the information in $x_s$ to a compact representation $h_s$ by:

$$h_s = f_{MLP}(x_s)$$

where $f_{MLP}(\cdot)$ can be multiple layers of fully connected network with the form $W_s x_s + b_s$, with $W_s$ and $b_s$ being the model parameters to be trained, in accordance with aspects of the present invention. In some embodiments, output $h_s$ will be a compact representation of the static features (e.g., DNN features 507), which can be integrated with the representations from temporal channels for prediction, in accordance with aspects of the present invention.

In various embodiments, a temporal channel 514 can include a plurality of Long Short Term Memory (LSTM) layers 515A, 515B, 515C for processing temporal feature inputs 508A, 508B, 508C, with the temporal feature inputs 508A, 508B, 508C being represented by a sequence of vectors $x_1, x_2, \ldots, x_T$, respectively. The LSTM layers can output a sequence of compact representations 513, 517, 512, 525 $h_0, h_1, h_2, \ldots, h_T$, respectively, by:

$$h_1, \ldots, h_T = f_{LSTM}(x_1, \ldots, x_T)$$

where $f_{LSTM}(\cdot)$ can have multiple layers of LSTM units, which contains trainable model parameters. Also, the LSTM units can be extended to bi-directional LSTM to encode information from both temporal directions in accordance with various embodiments of the present invention.

In some embodiments, on top of the LSTM layers 515A, 515B, 515C, compact representations 513, 517, 512, 525 $h_0, h_1, h_2, \ldots, h_T$, respectively, can be sent to an attention layer 519, 523, 527 for combination. The attention layer 519, 523, 527 can calculate a temporal importance score, i.e., attention weight at, in blocks 519, 523, 527, for each time step by $$e_t = w_\alpha \tanh(W_\alpha h_t) \text{ for } t = 1, \ldots, T$$

$$\alpha_t = softmax(e_t) \text{ for } t = 1, \ldots, T$$

where $W_\alpha$ and $w_\alpha$ are model parameters to learn. After this step, $$\sum_{t=1}^{T} \alpha_t = 1.$$

Then, all compact temporal representations can be combined (e.g., using a Hadamard product in blocks 529, 531, 533) through the attention weights 519, 523, 527 by:

$$h_d = \sum_{t=1}^{T} \alpha_t h_t$$

where $h_d$ is the compact representation for all temporal features 535 $x_1, \ldots, x_T$, and is the output of the temporal channel, in accordance with aspects of the present invention.

In various embodiments, after the static and temporal representations $h_s$ and $h_d$ are obtained from the static channel 512 and temporal channel 514, the prediction layer 509 can concatenate them and compute the probability of events using an MLP by:

$$\hat{y} = f_{MLP}([h_s, h_d])$$

where $\hat{y}$ is a score which indicates the probability of the incidence of a medical event. The predicted probability score can be output in block 511, in accordance with aspects of the present invention.

Figure 6:
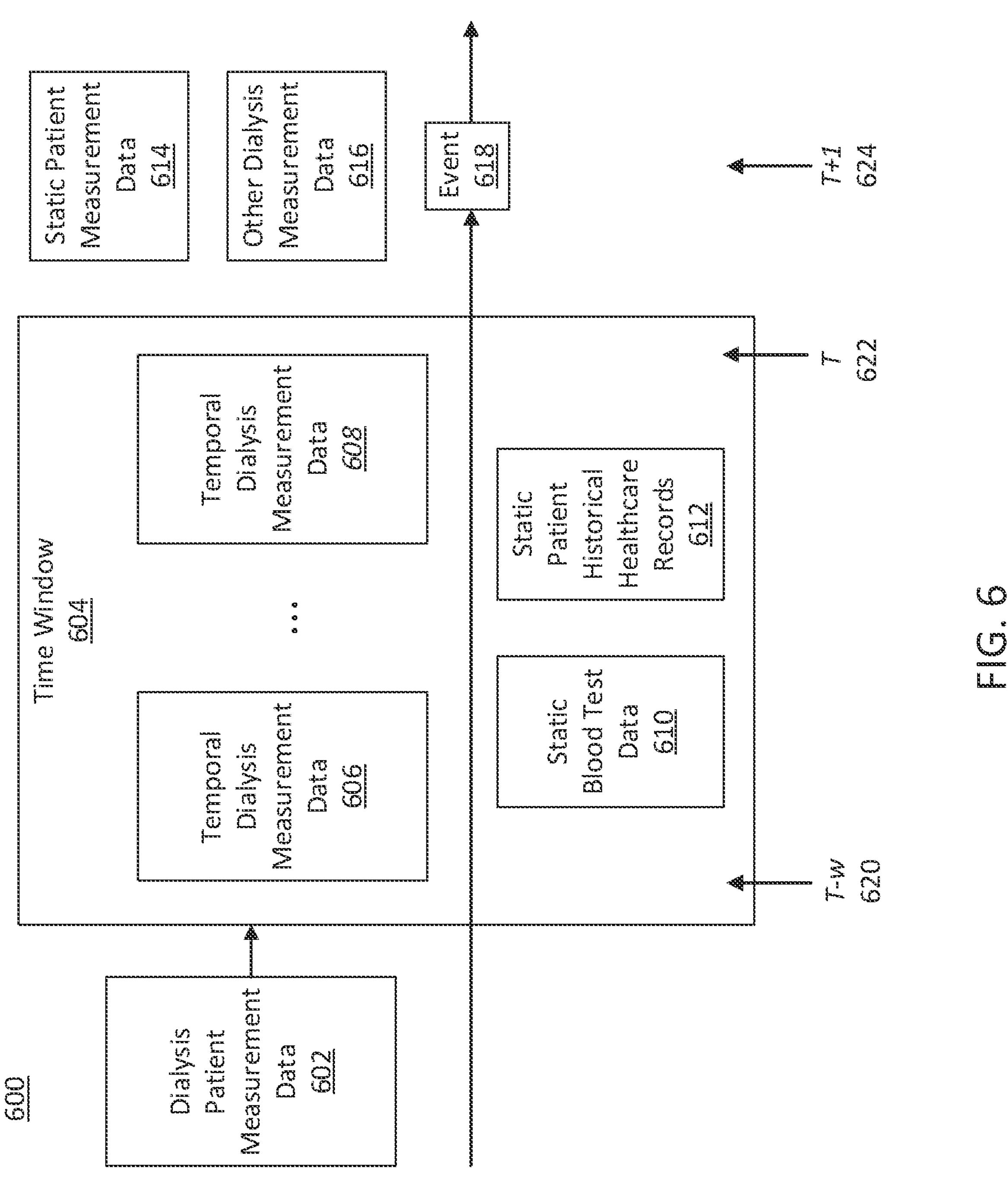
FIG. 6 shows a diagram of a method for predicting disease treatment events using a personalized dual-channel combiner network (P-DCCN) preprocessing component, in accordance with an embodiment of the present principles.

Referring now to FIG. 6, with continued reference to FIG. 5A, a diagram 600 of a method for predicting disease treatment events using a personalized dual-channel combiner network (P-DCCN) preprocessing component 504 is illustratively depicted in accordance with an embodiment of the present principles.

In accordance with embodiments of the present invention, the diagram 600 illustrates a segmentation process over a time window 604 with reference to dialysis treatment measurements and data. Historical dialysis patient measurement data can be input in block 602, and temporal dialysis measurement data can be measured and/or analyzed in blocks 606 and 608 over time during a dialysis treatment. Static blood test data 610 and static patient historical healthcare records data 612 can be utilized as input, in addition to static, real-time patient measurement data 614 and/or other dialysis measurement data 616 for prediction of a future medical event 618, in accordance with aspects of the present invention.

In some embodiments, each time window 604 can generate a sample X from time step T−w 620 to time step T 622, and can associate it with an event label Y in block 618 at time step T+1 624, in accordance with aspects of the present invention. This association can generate samples which focus on the features in the closest dates to a future event, and as different parts have different frequencies, all dialysis measurements in the time window 604 can be included, while the blood test measurements 610 on the closest date to the time window can also be included. The time window can slide from the beginning of the date to the end of the date (e.g., time period of dialysis treatment, full day, etc.) in the records to generate multiple samples.

After samples are generated, the preprocessing component 504 can normalize all samples using a Gaussian normalization method such that the features of the training samples have mean of 0 and variance of 1, which improves accuracy and stability of the computing algorithm of the P-DCNN computing component 518, in accordance with aspects of the present invention. For testing samples, they can be normalized by using the mean and variance obtained from the training data, and the normalized samples can be sent to the next component (e.g., model storage component 520) for further model training and testing, in accordance with aspects of the present invention. In practice, some of the dialysis measurements can be evaluated on the same date for which event is to be predicted. These measurements (e.g., liquid temperature, hourly water removal rate, target amount of water removal, dry weight, weight after last dialysis treatment, time before dialysis weight measurement, gain of this time period, etc.) can be evaluated immediately before the dialysis starts, and thus can be included as static features 614 for further processing, in accordance with aspects of the present invention.

Figure 7:
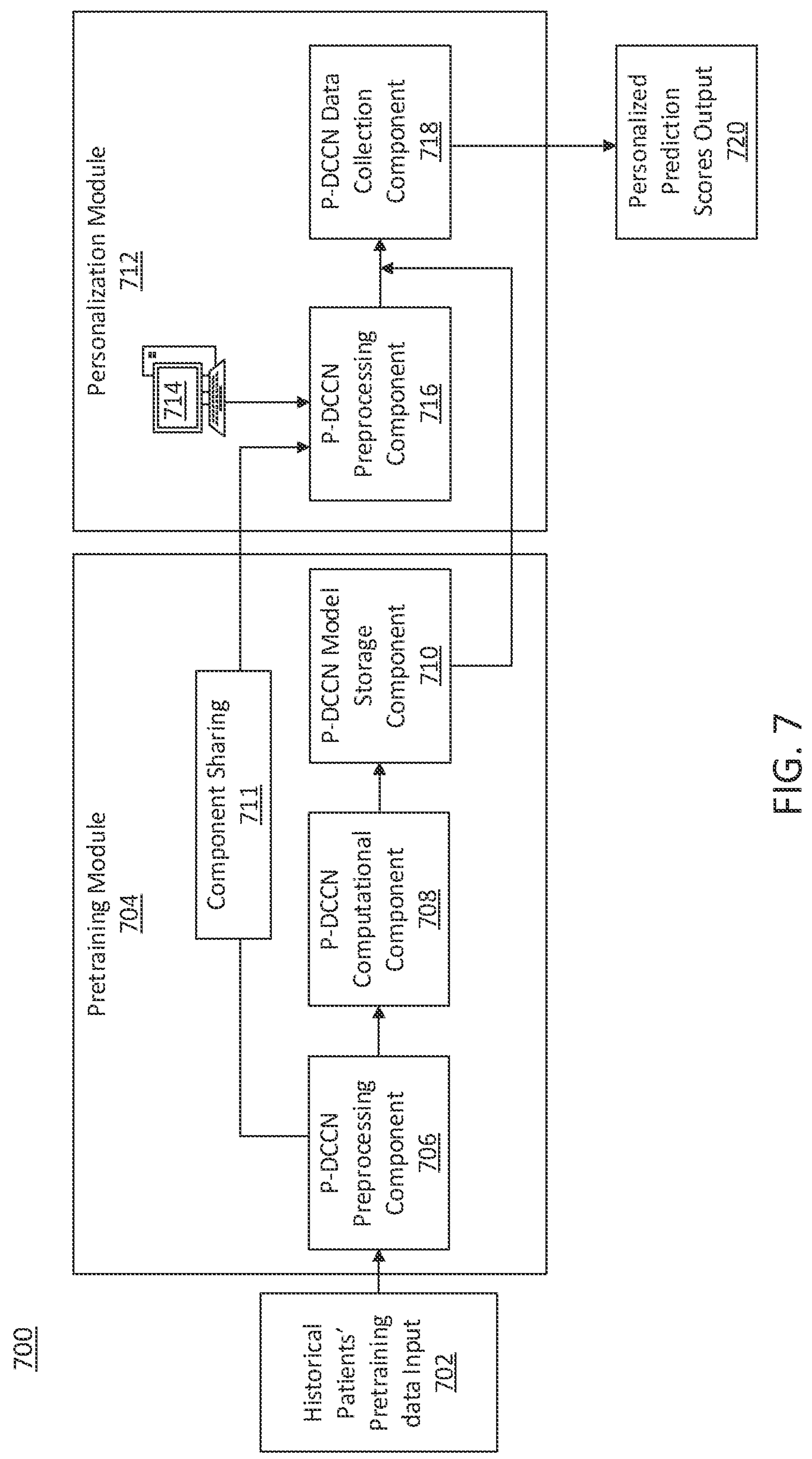
FIG. 7 shows a high-level block/flow diagram of a system/method for predicting disease treatment events using a personalized dual-channel combiner network (P-DCCN), in accordance with an embodiment of the present principles.

Referring now to FIG. 7, a high-level block/flow diagram of a system/method 700 for predicting disease treatment events using a personalized dual-channel combiner network (P-DCCN) is illustratively depicted in accordance with an embodiment of the present principles.

In accordance with various embodiments, historical patients' pretraining data can be input in block 702 into a pretraining module 704. The pretraining data 702 (e.g., historical recording data of a plurality of patients) can be input to a P-DCCN data preprocessing component 706 and can output normalized samples as the pre-training set, in accordance with aspects of the present invention. The normalized samples from block 706 can be sent to a P-DCCN computational component 708 for updating P-DCCN parameters, and can output the pre-trained P-DCCN, and the pretrained P-DCCN from 708 can be sent to a model storage component 710 for future deployment and/or personalization from local machines, in accordance with aspects of the present invention.

In an embodiment, using a personalization module 712, a comparatively small amount of a particular patient's historical medical data (e.g., as compared to the full medial historical record of a patient) can be input from a local machine 712 into a P-DCCN preprocessing component 716, which can output normalized samples as a finetuning set and be sent to a P-DCCN data collection component 718, in accordance with aspects of the present invention. The pre-trained P-DCCN from the model storage component 710 can be sent to the P-DCCN personalization module 712, and be utilized by the P-DCCN data collection component 718 for generating personalized prediction scores output in block 720, in accordance with aspects of the present invention. In some embodiments, finetuning the model parameters of the pre-trained P-DCCN can be performed by a plurality of training iterations using the finetuning dataset, and the finetuned P-DCCN can be utilized for generating personalized prediction scores 9 in block 720 using the personal data from one or more local machines 714, in accordance with aspects of the present invention.

Figure 8:
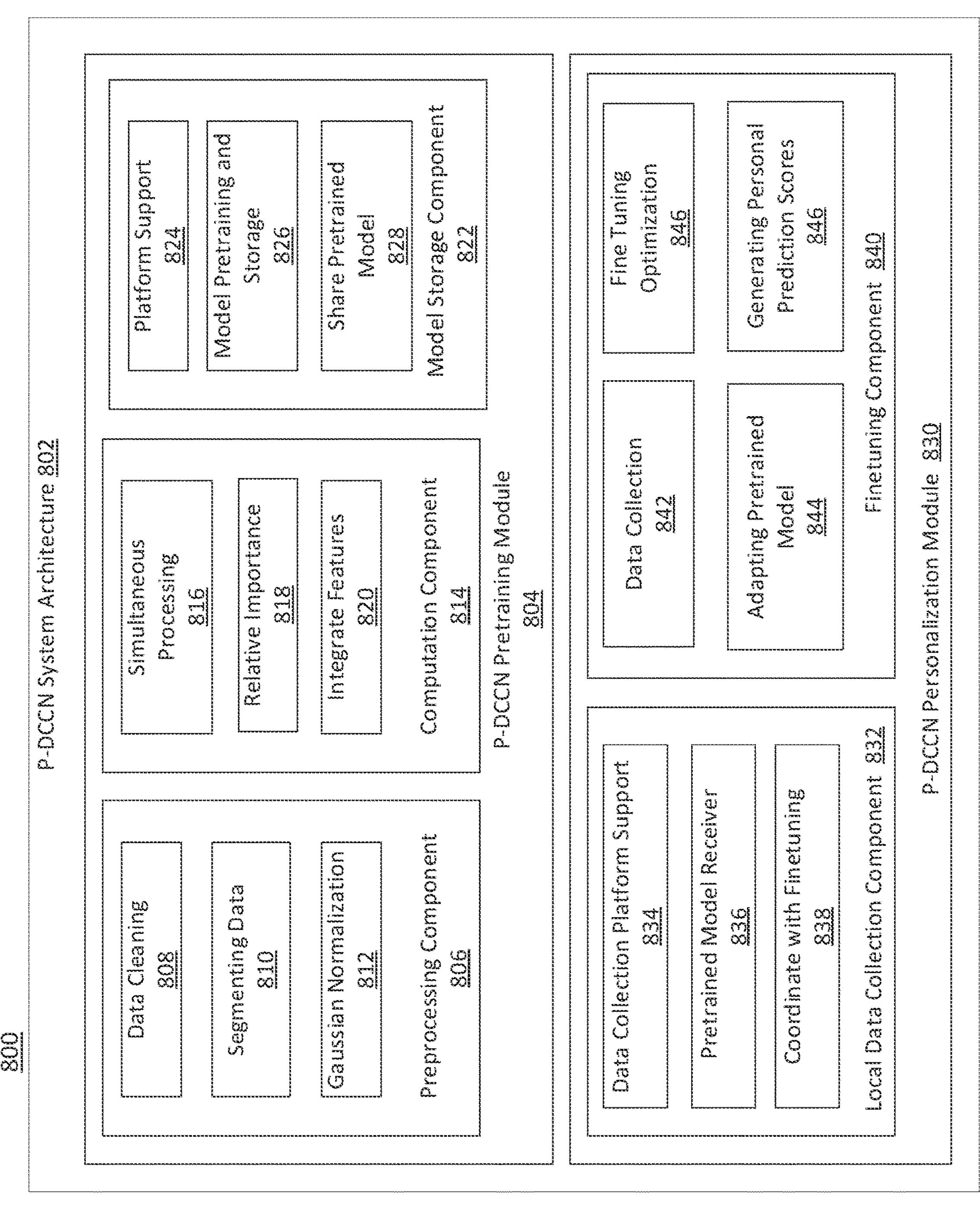
FIG. 8 shows a block/flow diagram of a system/method for predicting disease treatment events using a personalized dual-channel combiner network (P-DCCN), in accordance with an embodiment of the present principles.

Referring now to FIG. 8, a block/flow diagram of a system/method 800 for predicting disease treatment events using a personalized dual-channel combiner network (P-DCCN) is illustratively depicted in accordance with an embodiment of the present principles.

In accordance with embodiments of the present invention, a system architecture of a P-DCCN system 802 is provided. A P-DCNN pretraining module 804 can include a P-DCCN preprocessing component 806, a P-DCNN computational component 814, and a model storage component 822. In some embodiments, the P-DCNN pretraining module 804 can be configured for data cleaning and imputation to improve historical data quality in block 808, for segmenting recording data and generating time series samples in block 810, and/or for performing Gaussian normalization of data samples for stability of computation in block 812, in accordance with aspects of the present invention.

In some embodiments, the P-DCNN computational component 814 can include a dual channel neural network (DCNN) for processing static features and temporal features of different frequencies simultaneously in block 816, an attention mechanism in temporal channels to learn relative importance of different time steps during integration for performance improvement and interpretation in block 818, and/or a combination layer to integrate static features and temporal features for computing an event prediction score in block 820. In some embodiments, the P-DCCN model storage component 822 can be configured for platform support for running the preprocessing component 806 and the computation component 814 in block 824, for model pretraining, collection and storage in block 826, and/or for efficient communication with local machines for sharing pretrained models received as input in block 828, in accordance with aspects of the present invention.

In accordance with various embodiments, a P-DCCN personalization module 830 can include a P-DCCN local data collection component 832 and a P-DCCN finetuning component 840. The local data collection component 832 can be configured for platform support for timely recording and collection of new data from medical treatment (e.g., dialysis) sessions in block 834, for efficient communication with the model storage component 822 for exchanging of data, including receiving the pretrained model from the model storage component 822, and to coordinate the running of the finetuning component 840 with the collected data from the local data collection component 832, in accordance with aspects of the present invention.

In some embodiments, the finetuning component 840 can be configured for collecting the pretrained model and finetuning data in block 842, for comparatively fast adaptation of the pretrained model to the finetuning data using a few-shot learning strategy in block 844, for model finetuning using a regression objective function and/or a gradient optimization algorithm in block 846, and for generation of personalized prediction scores based on new input data from local machines in block 846, in accordance with aspects of the present invention.

Figure 9:
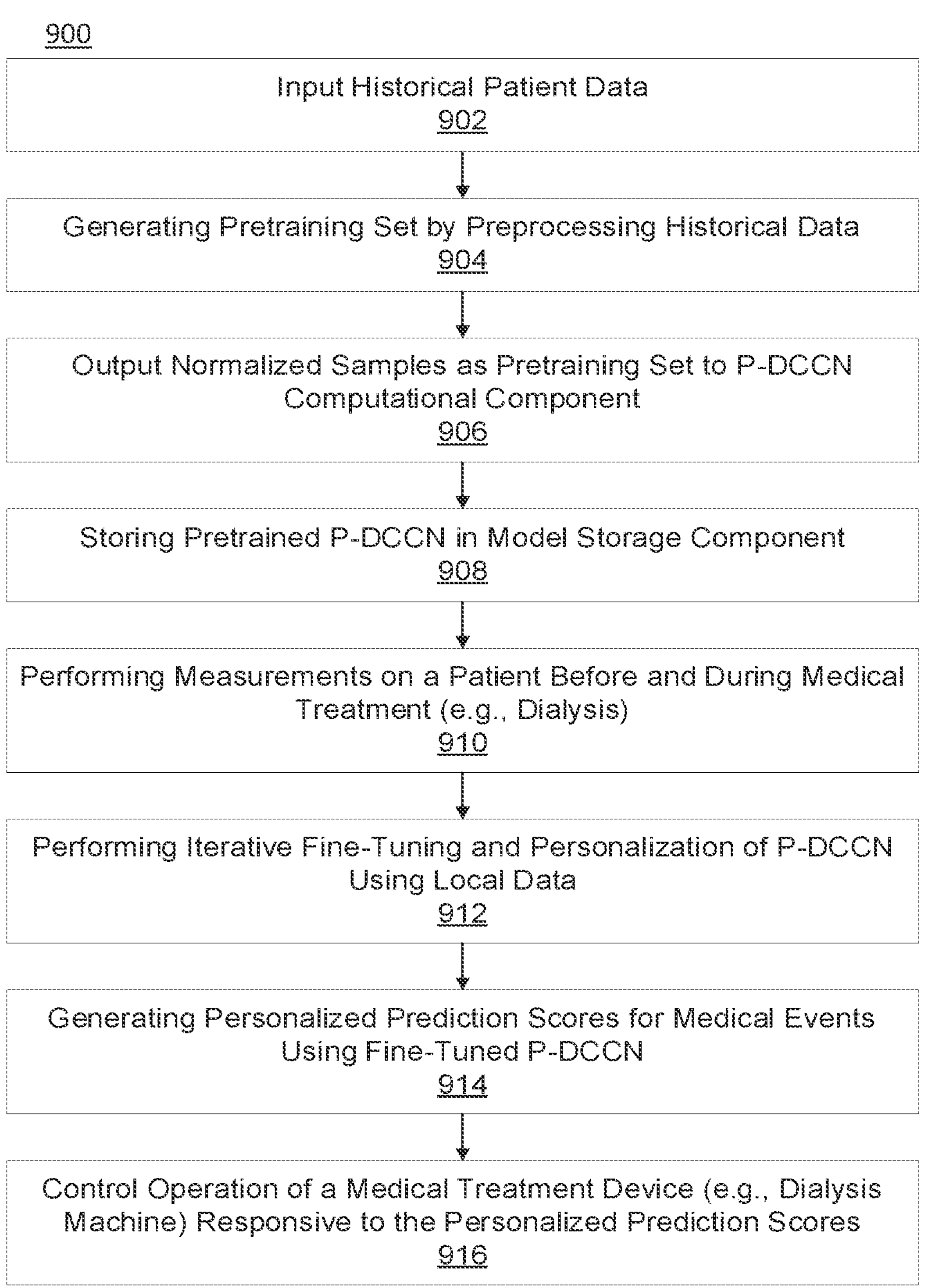
FIG. 9 shows a block/flow diagram of a method for predicting disease treatment events using a personalized dual-channel combiner network (P-DCCN), in accordance with an embodiment of the present principles.

Referring now to FIG. 9, a block/flow diagram 900 of a method for predicting disease treatment events using a personalized dual-channel combiner network (P-DCCN) is illustratively depicted in accordance with an embodiment of the present principles.

In accordance with various embodiments, historical patients' data can be input in block 902, and a pretraining set can be generated by preprocessing the historical patients' data in block 904. Normalized samples can be output as a pretraining set to a P-DCCN computational component in block 906, and the pretrained P-DCCN can be stored in a model storage component in block 908, in accordance with aspects of the present invention. In block 910, measurements (e.g., blood pressure, heart rate, etc.) can be taken of a patient before, during, and/or after a medical treatment (e.g., dialysis), and iterative finetuning and personalization of the P-DCNN can be performed based on the measurements from block 910 and other data stored on local machines in block 912. In block 914, personalized prediction scores can be generated for future medical events for particular patients using the finetuned P-DCCN, in accordance with aspects of the present invention. In block 916, a controller (e.g., automatic or manual) can be utilized to control operation of a medical treatment device (e.g., dialysis machine) and/or a plurality of measurement devices (e.g., blood pressure monitor, heart rate monitor, etc.) responsive to the personalized prediction scores generated in block 914, in accordance with aspects of the present invention.

Figure 10:
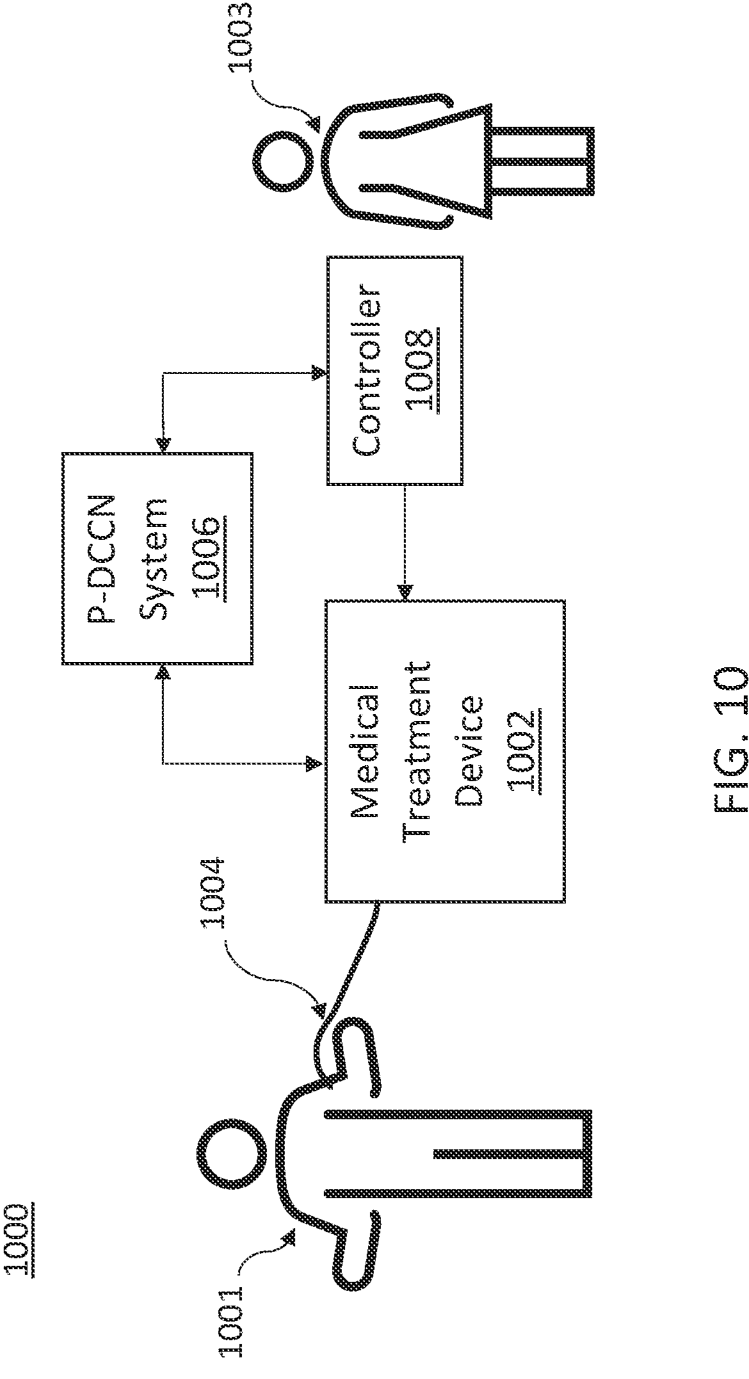
FIG. 10 shows a high-level diagram of a system for conducting medical treatment on a patient, predicting disease treatment events, and monitoring and collecting data from a patient during treatment using a personalized dual-channel combiner network (P-DCCN), in accordance with an embodiment of the present principles.

Referring now to FIG. 10, a high-level diagram of a system 1000 for conducting medical treatment on a patient, predicting disease treatment events, and monitoring and collecting data from a patient during treatment using a personalized dual-channel combiner network (P-DCCN) is illustratively depicted in accordance with an embodiment of the present principles.

In accordance with various embodiments of the present invention, a patient 1001 can be connected to a medical treatment and/or measurement device 1002 (e.g., dialysis machine, an electrocardiogram (EKG) machine, blood pressure monitor, etc.) for receiving a medical treatment by a medical professional 1003. Prior to the medical treatment, a P-DCCN system 1006 can be employed for prediction of potential medical events that may occur during the treatment using the medical treatment and/or measurement device 1002, in accordance with aspects of the present invention. The P-DCCN system 106 can be integrated (e.g., built-in) into the medical treatment and/or measurement device 1002 or can be attached via a port (e.g., USB, Ethernet, etc.) to the medical treatment and/or measurement device 1002 such that real-time measurements of the patient 1001 can be taken not only prior to, but also during the treatment for iterative predicting of potential medical events by the P-DCCN system 1006 in real time. The medical professional 1003 can utilize a controller (e.g., wired, remote, etc.) to control operation of the medical treatment and/or measurement device 1002 responsive to the event predictions output in real-time by the P-DCCN system, in accordance with aspects of the present invention.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer implemented method for predicting an occurrence of a medical event for a patient using a trained neural network, comprising:

preprocessing received historical patient data for a plurality of patients to generate a plurality of normalized training samples;

pretraining a personalized deep convolutional neural network (P-DCCN) by updating of model parameters using a multi-layer perceptron (MLP) prediction layer that combines outputs of a static channel that generates compact static representations of the normalized training samples and a temporal channel of the P-DCCN that combines compact temporal representations of the normalized training samples based on attention weights of the compact temporal representations for each time step of the normalized training samples;

storing the pretrained model in a remote server for utilization for personalization by a local machine during a preparation time period for a medical treatment;

generating a normalized finetuning set as output from the P-DCCN by processing input personal data for the patient from the local machine;

iteratively finetuning the model parameters of the P-DCCN by performing a plurality of pretraining iterations for the P-DCCN sent to the local machine using the generated normalized finetuning set to increase prediction accuracy of the P-DCCN with data limited to personalized patient data obtained from the local machine;

generating a personalized prediction score for future medical events for the patient using the P-DCCN; and controlling an operation of a medical treatment device responsive to the personalized prediction score for future medical events.

2. The method of claim 1, wherein the P-DCCN is finetuned by optimizing using a regression loss function as follows:

$$l = \frac{1}{N}\sum_{i=1}^{N} \|\hat{y}_i - y_i\|_2^2 + \lambda\|\theta\|_2^2$$

where $y_i$ is a true indicator of an incidence of an event for an i-th sample in the training samples, $\hat{y}_i$ is a predicted score for the i-th sample, N is a total number of the training samples, θ represents the model parameters, λ is a hyperparameter which controls a regularization on the model parameters to avoid overfitting during the training.

3. The method of claim 1, wherein a static channel is utilized for processing static and first temporal features, and a temporal channel is utilized for processing second temporal features having higher frequency compared to the first temporal features.

4. The method of claim 3, wherein the static channel includes a multilayer perceptron (MLP) configured to encode information in static features $x_s$ to a compact representation of the static features $h_s$ by:

$$h_s = f_{MLP}(x_s)$$

where $f_{MLP}(\cdot)$ represents multiple layers of a fully connected network with the form $W_s x_s + b_s$, with $W_s$ and $b_s$ being model parameters to be trained.

5. The method of claim 3, wherein the temporal channel includes a plurality of long short term memory (LSTM) layers for processing the temporal features, represented by a sequence of vectors $x_1, \ldots, x_T$, to output a sequence of compact representations $h_1, \ldots, h_T$ by:

$$h_1, \ldots, h_T = f_{LSTM}(x_1, \ldots, x_T)$$

where $f_{LSTM}(\cdot)$ includes multiple layers of LSTM units, which include trainable model parameters.

6. The method of claim 1, further comprising computing a probability of an incidence of a medical event by concatenating static and temporal representations $h_s$ and $h_d$, received from a static channel and a temporal channel, respectively, and computing the probability using a multi-layer perceptron (MLP) by:

$$\hat{y} = f_{MLP}([h_s, h_d])$$

where $\hat{y}$ is a score which indicates the probability of the incidence of the medical event.

7. The method of claim 1, further comprising generating, during the preparation time period, a recommendation for decision making by a medical professional, the recommendation identifying one or more treatment parameter adjustments based on the personalized prediction score.

8. A system for predicting an occurrence of a medical event for a patient using a trained neural network, comprising:

a processor operatively coupled to a computer-readable storage medium, the processor being configured for:

preprocessing received historical patient data for a plurality of patients to generate a plurality of normalized training samples;

pretraining a personalized deep convolutional neural network (P-DCCN) by updating of model parameters using a multi-layer perceptron (MLP) prediction layer that combines outputs of a static channel that generates compact static representations of the normalized training samples and a temporal channel of the P-DCCN that combines compact temporal representations of the normalized training samples based on attention weights of the compact temporal representations for each time step of the normalized training samples;

storing the pretrained model in a remote server for utilization for personalization by a local machine during a preparation time period for a medical treatment;

generating a normalized finetuning set as output from the P-DCCN by processing input personal data for the patient from the local machine;

iteratively finetuning the model parameters of the P-DCCN by performing a plurality of pretraining iterations for the P-DCCN sent to the local machine using the generated normalized finetuning set to increase prediction accuracy of the P-DCCN with data limited to personalized patient data obtained from the local machine;

generating a personalized prediction score for future medical events for the patient using the P-DCCN; and controlling an operation of a medical treatment device responsive to the personalized prediction score for future medical events.

9. The system of claim 8, wherein the P-DCCN is finetuned by optimizing using a regression loss function as follows:

$$l = \frac{1}{N}\sum_{i=1}^{N} \|\hat{y}_i - y_i\|_2^2 + \lambda\|\theta\|_2^2$$

where $y_i$ is a true indicator of an incidence of an event for an i-th sample in the training samples, $\hat{y}_i$ is a predicted score for the i-th sample, N is a total number of the training samples, θ represents the model parameters, λ is a hyperparameter which controls a regularization on the model parameters to avoid overfitting during the training.

10. The system of claim 8, wherein the preprocessing received historical patient data for a plurality of patients further comprises segmenting recording data and generating time series samples.

11. The system of claim 8, wherein a static channel is utilized for processing static and first temporal features, and a temporal channel is utilized for processing second temporal features having higher frequency compared to the first temporal features.

12. The system of claim 11, wherein the static channel includes a multilayer perceptron (MLP) configured to encode information in static features $x_s$ to a compact representation of the static features $h_s$ by:

$$h_s = f_{MLP}(x_s)$$

where $f_{MLP}(\cdot)$ represents multiple layers of a fully connected network with the form $W_s x_s + b_s$, with $W_s$ and $b_s$ being model parameters to be trained.

13. The system of claim 11, wherein the temporal channel includes a plurality of long short term memory (LSTM) layers for processing the temporal features, represented by a sequence of vectors $x_1, \ldots, x_T$, to output a sequence of compact representations $h_1, \ldots, h_T$ by:

$$h_1, \ldots, h_T = f_{LSTM}(x_1, \ldots, x_T)$$

where $f_{LSTM}(\cdot)$ includes multiple layers of LSTM units, which include trainable model parameters.

14. The system of claim 8, wherein the processor is further configured for computing a probability of an incidence of a medical event by concatenating static and temporal representations $h_s$ and $h_d$, received from a static channel and a temporal channel, respectively, and computing the probability using a multilayer perceptron (MLP) by:

$$\hat{y} = f_{MLP}([h_s, h_d])$$

where $\hat{y}$ is a score which indicates the probability of the incidence of the medical event.

15. A non-transitory computer-readable storage medium comprising a computer-readable program for predicting an occurrence of a medical event for a patient using a trained neural network, wherein the computer-readable program when executed on a computer causes the computer to perform the steps of:

preprocessing received historical patient data for a plurality of patients to generate a plurality of normalized training samples;

pretraining a personalized deep convolutional neural network (P-DCCN) by updating of model parameters using a multi-layer perceptron (MLP) prediction layer that combines outputs of a static channel that generates compact static representations of the normalized training samples and a temporal channel of the P-DCCN that combines compact temporal representations of the normalized training samples based on attention weights of the compact temporal representations for each time step of the normalized training samples;

storing the pretrained model in a remote server for utilization for personalization by a local machine during a preparation time period for a medical treatment;

generating a normalized finetuning set as output from the P-DCCN by processing input personal data for the patient from the local machine;

iteratively finetuning the model parameters of the P-DCCN by performing a plurality of pretraining iterations for the P-DCCN sent to the local machine using the generated normalized finetuning set to increase prediction accuracy of the P-DCCN with data limited to personalized patient data obtained from the local machine;

generating a personalized prediction score for future medical events for the patient using the P-DCCN; and controlling an operation of a medical treatment device responsive to the personalized prediction score for future medical events.

16. The computer-readable storage medium of claim 15, wherein the P-DCCN is finetuned by optimizing using a regression loss function as follows:

$$l = \frac{1}{N}\sum_{i=1}^{N} \|\hat{y}_i - y_i\|_2^2 + \lambda\|\theta\|_2^2$$

where $y_i$ is a true indicator of an incidence of an event for an i-th sample in the training samples, $\hat{y}_i$ is a predicted score for the i-th sample, N is a total number of the training samples, θ represents the model parameters, λ is a hyperparameter which controls a regularization on the model parameters to avoid overfitting during the training.

17. The computer-readable storage medium of claim 15, wherein a static channel is utilized for processing static and first temporal features, and a temporal channel is utilized for processing second temporal features having higher frequency compared to the first temporal features.

18. The computer-readable storage medium of claim 17, wherein the static channel includes a multilayer perceptron (MLP) configured to encode information in static features $x_s$ to a compact representation of the static features $h_s$ by:

$$h_s = f_{MLP}(x_s)$$

where $f_{MLP}(\cdot)$ represents multiple layers of a fully connected network with the form $W_s x_s + b_s$, with $W_s$ and $b_s$ being model parameters to be trained.

19. The computer-readable storage medium of claim 17, wherein the temporal channel includes a plurality of long short term memory (LSTM) layers for processing the temporal features, represented by a sequence of vectors $x_1, \ldots, x_T$, to output a sequence of compact representations $h_1, \ldots, h_T$ by:

$$h_1, \ldots, h_T = f_{LSTM}(x_1, \ldots, x_T)$$

where $f_{LSTM}(\cdot)$ includes multiple layers of LSTM units, which include trainable model parameters.

20. The computer-readable storage medium of claim 19, further comprising computing a probability of an incidence of a medical event by concatenating static and temporal representations $h_s$ and $h_d$, received from a static channel and a temporal channel, respectively, and computing the probability using a multilayer perceptron (MLP) by:

$$\hat{y} = f_{MLP}([h_s, h_d])$$

where $\hat{y}$ is a score which indicates the probability of the incidence of the medical event.

* * * * *